United States Patent [19]
Kulisz et al.

[11] Patent Number: 5,512,032
[45] Date of Patent: Apr. 30, 1996

[54] NONSURGICAL INTRAURETHRAL BLADDER CONTROL DEVICE

[75] Inventors: Andre A. Kulisz; Valery Migachyov, both of St. Paul, Minn.

[73] Assignee: HK Medical Technologies, Inc., San Antonio, Tex.

[21] Appl. No.: 173,636

[22] Filed: Dec. 23, 1993

[51] Int. Cl.$^6$ .................................................. A61M 27/00
[52] U.S. Cl. ................................................. 600/29; 623/12
[58] Field of Search ................... 600/29–31; 623/11–12; 137/803, 403

[56] References Cited

U.S. PATENT DOCUMENTS

| | | | |
|---|---|---|---|
| 3,731,670 | 5/1973 | Loe | 600/30 |
| 3,812,841 | 5/1974 | Isaacson | 600/29 |
| 4,553,533 | 11/1985 | Leighton . | |
| 4,679,546 | 7/1987 | van Waalwijk van Doorn et al. . | |
| 4,934,999 | 6/1990 | Bader | 600/29 |
| 4,955,858 | 9/1990 | Drews | 604/8 |
| 4,968,294 | 11/1990 | Salama | 600/30 |
| 4,969,474 | 11/1990 | Schwarz | 128/885 |
| 5,007,894 | 4/1991 | Enhorning | 600/29 |
| 5,007,898 | 4/1991 | Rosenbluth et al. | 604/54 |
| 5,012,822 | 5/1991 | Schwarz | 128/885 |
| 5,041,092 | 8/1991 | Barwick | 600/29 X |
| 5,078,676 | 1/1992 | Bailly | 600/31 |
| 5,088,980 | 2/1992 | Leighton | 600/30 |
| 5,090,424 | 2/1992 | Simon et al. | 128/885 |
| 5,097,848 | 3/1992 | Schwarz | 128/885 |
| 5,112,306 | 5/1992 | Burton et al. | 604/101 |
| 5,114,398 | 5/1992 | Trick et al. | 600/29 |
| 5,123,428 | 6/1992 | Schwarz | 128/885 |
| 5,140,999 | 8/1992 | Ardito | 600/29 X |

*Primary Examiner*—Angela D. Sykes
*Attorney, Agent, or Firm*—Nawrocki, Rooney & Sivertson

[57] ABSTRACT

An improved self contained automatic bladder control device includes a valve assembly mount for releasibly receiving a valve assembly. The preferably cylindrical mount has a textured outer surface designed to interact with urethral tissue. Thus the mount can be placed nonsurgically into a urethra and in time it will be held against movement by the tissue interaction with the textured outer surface, yet the mount will still be removable without surgery. Two embodiments of valve assemblies are disclosed, each of which provides a sphincter-like operation of the bladder control apparatus. A first embodiment is designed to use Bernoulli's law to hold open the valve apparatus after a short period of muscle contraction. The second embodiment is designed to use the fact that the force generated by hydrostatic pressure is directly related to the area on which it impinges, to accomplish the desired valve holding period.

23 Claims, 3 Drawing Sheets

NONSURGICAL INTRAURETHRAL BLADDER CONTROL DEVICE

BACKGROUND OF THE INVENTION

1. Field of the Invention

The present invention generally relates to the field of medical devices and more particularly to bladder control devices, and still more particularly to an intraurethral bladder control apparatus commonly referred to as an artificial sphincter.

2. Description of the Prior Art

The use of various sphincter and bladder control devices is wide spread in the field of the present invention. The use of intraurethral valving apparatus is also well known in the art, as evidenced by, for example, U.S. Pat. Nos. 4,553,533; 4,679,546; 4,969,474; and 5,123,428. In general terms, it is the goal of the prior art and the present invention to provide a valving system for a patient's bladder, which system is placed directly in the urethra and adjacent the bladder. The valving system is ideally turned on by the patient and turned off when the bladder has ,been sufficiently emptied.

Some of the problems and disadvantages found in the prior art include: the need for surgical implantation and removal of the device in the urethra; the susceptibility of the device to leakage or to undesired valve openings; the failure of the valve device to stay open long enough to provide complete emptying of the bladder; and in some prior art devices the need for an additional external product, such as a magnet, to actuate the valve device.

SUMMARY OF THE INVENTION

The apparatus and method of this invention overcomes these potential disadvantages by providing an improved intraurethral bladder control apparatus which includes a valve assembly, and a valve assembly mount for releasably holding the assembly and adapted to be nonsurgically placed and releasably held in the urethra of a patient. The mount is provided with a textured outer surface to which urethral tissue will conform to hold the mount at a selected position therein. The valve assembly cooperates with apparatus in an inner chamber of the mount for releasable installation of the assembly. The mount is preferably generally cylindrical in shape with a generally cylindrical inner chamber or lumen where valve assembly holding apparatus is deployed.

Each of the preferred embodiments of the valve assembly has adjustment apparatus operable whether the assembly is in the valve assembly mount or not, for positioning the assembly and for setting desired values of the opening and closing the valve, and for a fail-safe mode which is a feature of each preferred embodiment.

Each preferred embodiment of the present invention also includes apparatus for assuring that once opened by the patient's own abdominal muscle contraction, the valve stays open for a sufficient time to empty the bladder, and then closes without further action by the patient. A first preferred embodiment includes a design to utilize Bernoulli's principle to provide a negative pressure that holds the valve open during fluid flow, and a second preferred embodiment is designed to utilize a valve area enlargement during fluid flow to keep the valve open.

BRIEF DESCRIPTION OF THE DRAWINGS

The above described as well as other objects and many of the attendant advantages of the present invention will be readily appreciated as they become better understood by reference to the following detailed description when considered in connection with the accompanying drawings, in which like reference numerals designate like parts throughout all figures:

FIG. 2 is another cross-sectional view of FIG. 1 taken along the line 2—2;

DETAILED DESCRIPTION OF THE PREFERRED EMBODIMENTS

Figure 8:
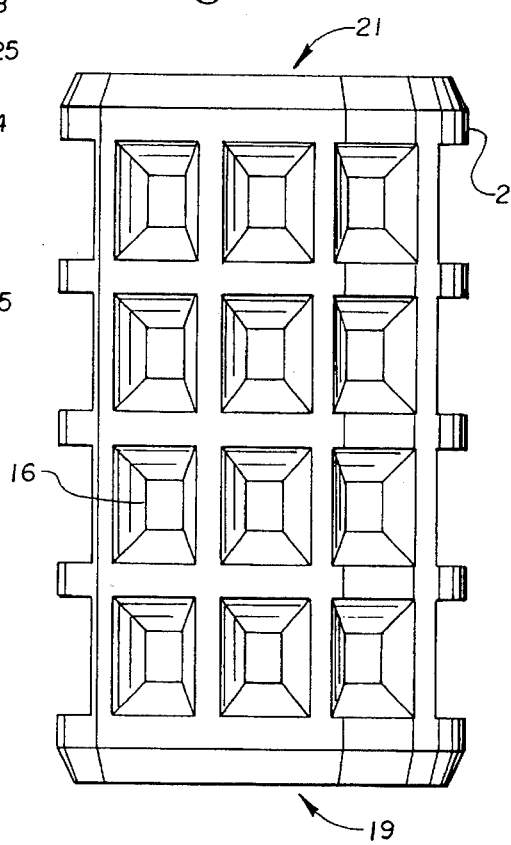
FIG. 8 is a plan view of the valve assembly mount of this invention.

Referring first to FIG. 8 there is shown a valve assembly mount 2 in the preferred form of a cylinder having a textured outer surface 16 designed to interact with urethral tissues such that mount 2 may be nonsurgically and releasibly positioned in a patient's urethra. Mount 2 includes a valve orifice indicated at 11 and adapted to be positioned adjacent the patient's bladder exit, and an assembly orifice indicated at 19 adapted to receive a valve assembly for internal mounting. As disclosed and more fully described in other figures of the drawings, the interior of mount 2 includes connection apparatus for releasibly and adjustably mounting a valve assembly. In practice, mount 2 is positioned in the patient's urethra first, left for a period of time to enable the urethra tissue to conform to the textured outer surface 16 of mount 2 to hold mount 2 securely in place, and then a valve assembly is mounted in mount 2.

Figure 9:
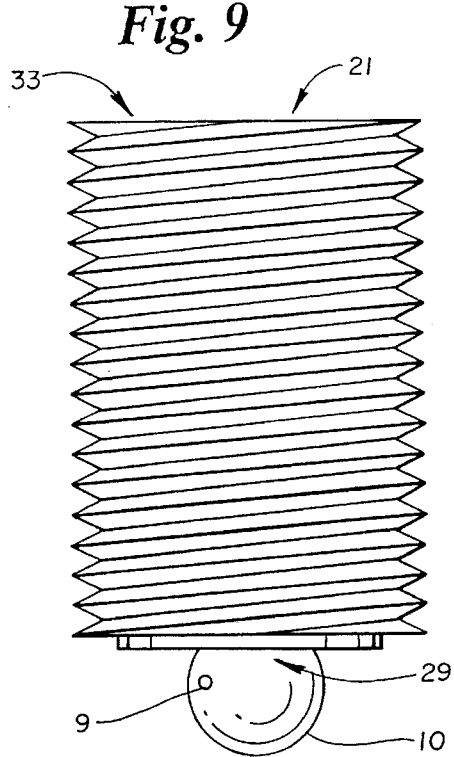
FIG. 9 is a plan view of a valve assembly of this invention.

In FIG. 9 there is shown a valve block 33 adapted to releasibly receive a valve apparatus in a manner fully described below with reference to other figures of the drawings. Block 33 is shown as preferably having a threaded outer surface designed to match a threaded inner surface (not shown in FIG. 8) of mount 2. Block 33 also has a valve orifice indicated at 21 for alignment adjacent to orifice 11 of mount 2, and an apparatus receiving orifice indicated at 29 for insertion of a valve apparatus.

As can be seen in FIG. 9, when a valve apparatus is in place within block 33, an adjustment device 10 having lock notches 9 will be available outside block 33. By using an appropriate adjustment tool (not shown) to lock into notches 9, device 10 may be rotated to make a plurality of adjustments more fully described below with reference to other figures of the drawings.

Figure 1:
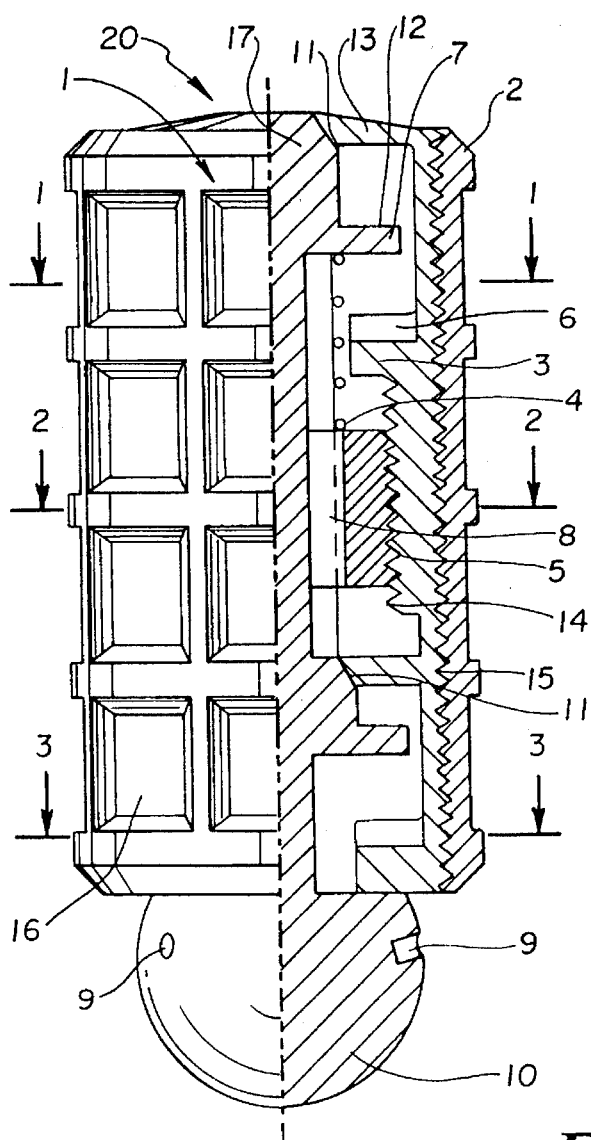
FIG. 1 is a partial sectional view of a first embodiment of the intraurethral bladder Control apparatus of this invention with the valve closed.

Referring now to FIG. 1 there is shown a first embodiment of the bladder control apparatus 1 of this invention, including cylindrical valve assembly mount 2 having textured outer surface 16 and a valve assembly 20 which is threaded into mount 2 by means of a connection thread 15. Valve assembly 20 includes a valve block 13, a valve 17, a valve orifice 11, a valve ring 7 having a valve area 12, a coiled spring or other biasing apparatus 4, a spacer 6, a stationary ring 3, a fluid passage 8, a bias adjustment apparatus 5, a thread 14 joining bias adjustment apparatus 5 to block 13, and adjustment device 10 having locking notches 9.

Figure 2:
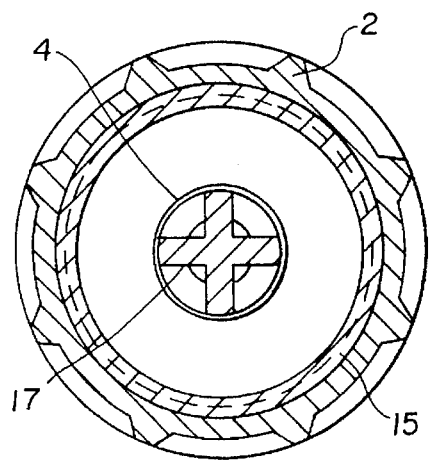
FIG. 2 is a cross-sectional view of FIG. 1 taken along the line 1—1.
Figure 3:
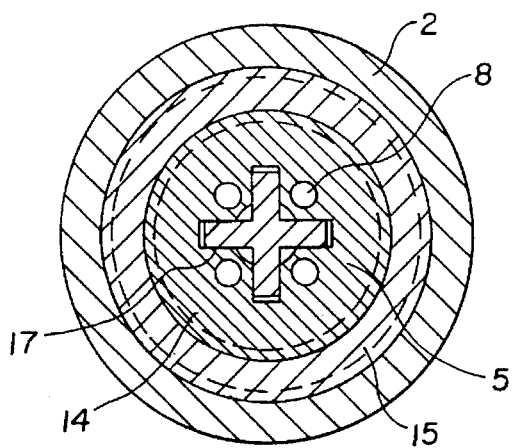
Figure 4:
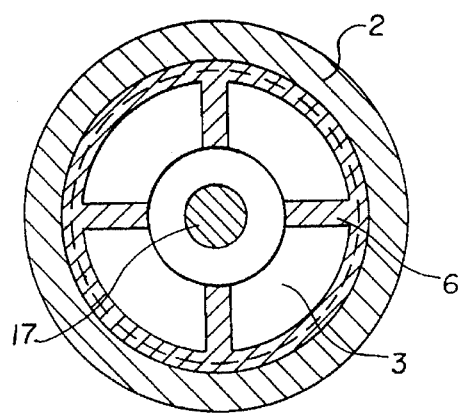
FIG. 4 is yet another cross-sectional view of FIG. 1 taken along the line 3—3.

The cross-sectional views of FIGS. 2, 3 and 4, respectively taken along the lines 1—1, 2—2 and 3—3, more clearly depict the inner structure of device 1 of FIG. 1, clarifying the positioning and formations of valve 17, spring coil biasing device 4, bias adjustment means 5 with thread 14, fluid passages 8, stationary ring 3 and spacers 6.

Figure 5:
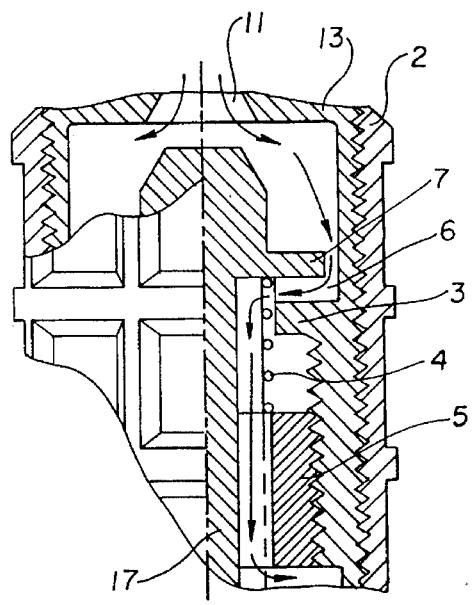
FIG. 5 is a partial sectional view of the embodiment of FIG. 1 with the valve open.

In FIG. 1 valve 17 is in the closed position in orifice 11, thus preventing the flow of urine fluids from the bladder. With reference to FIG. 5, valve 17 is shown in the open position, removed from orifice 11, and a plurality of lines with arrows depict the fluid flow path through valve block 13.

In practice, valve assembly mount 2 is first inserted into a urethra and allowed to, stay for a period of time (usually a few weeks) sufficient for the urethral tissue to conform to the textured outer surface 16 to thus essentially immobilize mount 2. After mount 2 is firmly held by the tissue, a valve assembly such as assembly 20 of FIG. 1 is inserted into the internal chamber or lumen of mount 2 where it is connected and adjusted.

Referring now to the first preferred embodiment of FIGS. 1–5 which utilize Bernoulli's principle to retain the valve in an open position, assume that assembly 20 has been mounted in the lumen of assembly mount 2 which has been immobilized in the patient's urethra in the manner described above. Block 13 is then adjusted within mount 2 such that orifice 11 passes through orifice 21, as shown in FIG. 8, to align with the output from the patient's bladder (not shown). As the bladder fills with urine, the resulting growth in the urine column exerts greater pressure on valve 17 through orifice 11 and at the same time the resulting growth in volume within the bladder stimulates the patient's need to void. To initiate the voiding process the patient need only contract the muscles of the lower abdominal cavity for a short period of a few seconds. This short period of contraction will increase the pressure on valve 17 long enough for it to move against the bias of spring 4 and thus begin the flow of urine through valve assembly 20 along the path shown by the arrows in FIG. 5.

As the urine flows in the path shown, valve 17 moves toward valve stop or rest 6. Rest 6 is a vertical element extending radially for separating the lower surface of valve ring 7 from stationary ring 3. The urine then flows around the edge of valve ring 7 and between the lower surface of ring 7 and stationary ring 3, such that a negative pressure is induced according to Bernoulli's principle between these two surfaces. This negative force overcomes the tension of spring 4 and holds ring 7 down against stop 6, thus holding valve 17 open, as long as a sufficient flow of urine is present. When the flow decreases below a sufficient amount, the negative force is decreased until the bias from spring 4 can again close valve 17 in orifice 11 to cut off the flow entirely.

The result of the actions as described in the preceding paragraph causes the desired holding pattern for the artificial sphincter device of this invention. That is, once valve assembly 20 has been opened by muscle contraction to allow fluid flow through block 13, the application of Bernoulli's law will automatically prevent closure of valve 17 without further muscle contraction until the bladder has emptied enough to significantly reduce the urine flow; and then the valve assembly will automatically close without further muscle effort. The patient's need to void will have been met by a simple, short initial contraction of the muscles of the lower abdominal cavity.

The force with which valve 17 is held closed or seated in orifice 11 is determined by the tension from spring 4, which may be any form of bias device. This tension or bias is adjusted by bias adjustment apparatus 5, best seen in FIGS. 1 and 3. To set the desired tension of coil 4, an adjustment tool (not shown) is passed through the urethra to grasp and lock into notches 9 of adjustment device 10, Device 10 is then selectively rotated which rotates valve 17 and bias adjustment means 5. The rotation of means 5 causes it to move up or down thread 14 to increase or decrease the tension of spring 4.

The rotation of valve 17 in the direction of reduced bias from coil 4 will eventually disable bladder control device 1 by removing valve 17 from is seat in orifice 11 to allow a free flow of fluid through block 13. Further rotation after reaching the point of free flow will cause rotation of block 13 to first change its positioning within mount 2 and eventually to cause it to disengage from mount 2 entirely. Replacement of block 13 into mount 2 is accomplished by simply reversing the direction of rotation of device 10.

The above description of the structure and operation of the preferred embodiment of FIGS. 1–3 which utilizes Bernoulli's law is applicable to patients who have a sufficiently rapid rate and volume of urine flow. These values can be clinically determined. If it is found that the patient does not meet the requirements for the use of the above described embodiment, the second preferred embodiment of this invention as described in FIGS. 6–7 can be used.

FIG. 6 again shows a valve assembly mount 2 in which a valve block 43 is removably positioned through use of threads 15. A valve 47 abuts against an orifice 41 and is maintained in the closed position by a coil spring or other bias device 4. In this embodiment valve 47 has a valve ring 27 with a valve surface area 42 significantly greater than the area of orifice 41. Coil 4 abuts against bias adjustment device 25 which is connected to block 43 via thread 44. Valve 47 is connected to adjustment device 10 which again carries locking notches 9. Fluid passages 28 are provided to pass urine through block 43 along a desired path.

Figure 6:
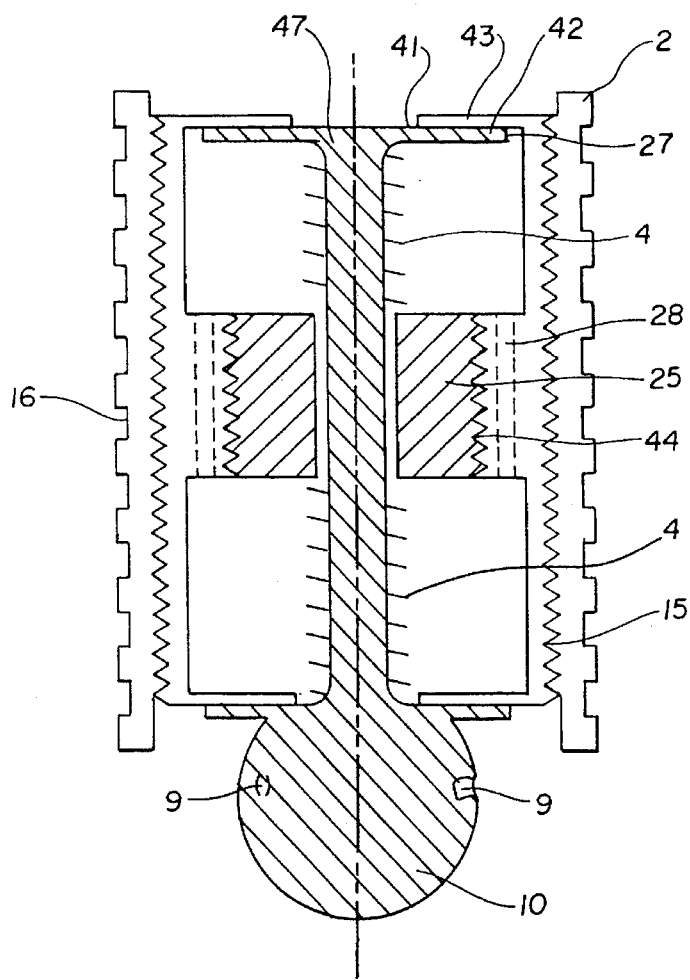
FIG. 6 is a cross-sectional view of a second embodiment of the apparatus of this invention with the valve closed.
Figure 7:
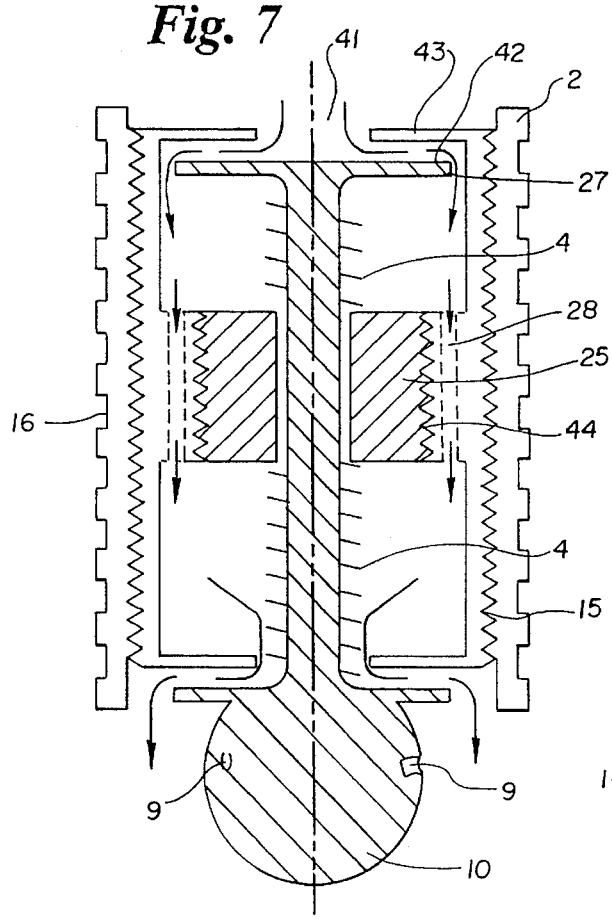
FIG. 7 is another cross-sectional view of the embodiment of FIG. 6 with the valve open.

In FIG. 6 valve 47 is shown as biased against orifice 43, thus closing valve block 43 to prevent urine flow. Referring now to FIG. 7 valve 17 is shown in the open position and the flow of urine through block 43 is depicted by the arrows. In operation, mount 2 will have first been secured in the patient's urethra in the nonsurgical, removable manner described above with regard to FIGS. 1–5. Thus the urethral tissue will have conformed to surface 16 to hold mount 2 in place. Block 43 will then be treaded into mount 2 to place orifice 41 in the urethra adjacent to the patient's bladder. As the bladder fills the urine column will place increased pressure on valve 47 through orifice 41, as well as causing a need to void in the patient. To initiate operation of the device of this embodiment of the present invention the patient again need only contract the muscles of the lower abdominal cavity for a few seconds. This short period of contraction will cause sufficient pressure for valve 47 to open against the tension of coil spring 4.

As soon as valve 47 opens, the urine flow through orifice 41 will impinge on the full surface area 42 of valve ring 27, and since this area is greater than the area of orifice 41, valve 47 will remain open even after the contractions are released, until the urine column has been reduced to an acceptable small amount. The basis of this embodiment is the known fact that force generated by hydrostatic pressure is directly related to the area of impingement, that is, Force=Pressure× Area. Thus valve ring 27 and orifice 41 can be designed to follow the fact that if valve area increases n times, the pressure may decrease n times, and the force exerted on the valve remain the same. By making ring 27 of sufficient surface area 42 relative to the area seen through orifice 41, valve 47 will be held open after muscle contraction ceases even in a patient with a relatively low flow rate through the urethra.

Valve 47 will remain open until the fluid pressure has dropped such that even the increased area is not enough to afford a multiple that will overcome the bias of coil 4, and then valve 47 will automatically be biased closed and remain closed until the bladder fills and the patient creates another contraction. Thus, as in the case of the first embodiment described above, this embodiment of the invention will also operate in a manner closely resembling the action of a normal sphincter muscle.

In both embodiments described above there are fail-safe measures designed into the bladder control device. By proper selection of the tension on the respective of valves 17 or 47 caused by bias apparatus 4, the valves can be made to open without muscle contraction as the pressure passes a certain level in the bladder. This can avoid serious problems caused by the increased bladder pressure should the patient not recognize the need to void or be unconscious, or the like. Further, again by proper adjustment of the bias spring, accidental turn-on of the bladder control device due to unexpected contractions, for example from a sneeze or cough. In general, if a proper spring tension is selected and the bladder is not overly full, valves 17 and 47 will remain seated until a contraction force of sufficient strength has been present for more than an instantaneous period of time, such as the time of a cough. This need for a short but sustained period of contraction prevents the device from entering its "automatic open" phase after an unexpected abrupt contraction.

Having thus described the preferred embodiments of the present invention, those of skill in the art will readily appreciate the other useful embodiments within the scope of the claims hereto attached.

I claim:

1. In an intraurethral bladder control apparatus including a valve assembly for controlling the flow of urine and a valve assembly mount for holding the valve assembly within a urethra, the improved valve assembly mount comprising:

means including a textured outer wall on the mount for interacting with urethral tissue to hold said bladder control apparatus within the urethra and provide non-surgical implantation and removal of the mount in the urethra the valve assembly including means for creating a holding force according to Bernoulli's principle responsive to a flow of fluid, and means responsive to the holding force to hold the valve assembly open.

2. The apparatus of claim 1 in which the valve assembly mount includes an inner chamber having valve assembly holding means for releasably holding the valve assembly in the chamber.

3. The apparatus of claim 2 in which the valve assembly includes adjustment control means for setting the pressures at which the valve assembly will open and close.

4. The apparatus of claim 3 including means for operating the adjustment control means for a point external to the urethra.

5. The apparatus of claim 2 in which the valve assembly includes: means responsive to an opening of the valve for increasing the area of fluid flow impingement; and means responsive to pressure from fluid flow impingement to hold the valve assembly open.

6. The apparatus of claim 1 or 5 in which the valve assembly includes adjustment control means for setting the pressures at which the valve assembly will open and close.

7. Bladder control apparatus comprising:
   a. a valve assembly mount adapted for intraurethral placement;
   b. means including a textured outer surface on the mount for holding said bladder control apparatus in contact with urethral tissue;
   c. a chamber in the amount;
   d. connection means in the chamber for receiving and releasibly holding a valve assembly;
   e. a valve assembly adapted to be connected to the connection means;
   f. a moveable valve in the valve assembly for opening and closing the assembly to fluid flow;
   g. bias means for biasing the valve closed;
   h. pressure means for holding the valve open in the presence of a fluid flow of a predetermined level;
   i. a first valve ring mounted on the moveable valve and within a fluid flow path within the valve assembly;
   j. a second valve ring mounted on the connection means and within the fluid flow path;
   k. a spacer mounted in the valve assembly for maintaining a minimum spaced between the first and second rings; and
   l. the first and second rings cooperating in the presence of fluid flow of a predetermined level to induce a negative force according to Bernoulli's principle for holding the moveable valve open.

8. The apparatus of claim 7 in which the pressure sensing means comprises:
   a. a valve ring mounted on the moveable valve and having a predetermined surface area;
   b. means for exposing a first portion of the surface area to hydrostatic pressure when the moveable valve is closed; and
   c. means for exposing a second and larger portion of the surface area to the hydrostatic pressure when the moveable valve is open for holding the valve open during fluid flow at a predetermined level.

9. The apparatus of claims 7 or 8 in which the valve assembly includes adjustment control means for adjusting the bias of the bias control means to set the pressures at which the valve assembly will open and close.

10. the apparatus of claim 9 including means for operating the adjustment control means from a point external to the body.

11. The apparatus of claims 7 or 8 including fail-safe means for preventing the movement of the moveable valve due to abrupt changes in hydrostatic pressure.

12. The apparatus of claim 7 including fail-safe means for preventing the opening of the valve assembly due to abrupt changes in hydrostatic pressure.

13. Intraurethral bladder control apparatus comprising:
   a. a housing having an outer surface and an inner chamber;
   b. a valve assembly having an input orifice and an output orifice, and a fluid flow path between the input and output orifices;
   c. a moveable valve mounted in the valve assembly and moveable between a closed location adjacent the input orifice and an open position spaced from the input orifice;

d. valve closing means for normally holding the valve in the closed position and responsive to a predetermined pressure to allow movement of the valve to the open position; and e. valve control means mounted in the valve assembly fluid flow path and responsive to the flow of fluid to hold the valve in the open position when the fluid flow rate is above a predetermined rate.

14. The apparatus of claim 13 in which the valve control means comprises: means for inducing a negative pressure under Bernoulli's principle in the presence of a fluid flow.

15. The apparatus of claim 13 in which the valve control means comprises: means having a predetermined surface area and means for increasing the portion of the surface area within the fluid flow path when the valve is in the open position, to hold the valve in the open position which the fluid pressure is above a predetermined level.

16. The apparatus of claims 13, 14 or 15 in which the valve closing means comprises: a spring and spring tension adjustment means.

17. The apparatus of claims 13, 14 or 15 including safety means for preventing movement of the valve to the open position due to momentary changes in bladder pressure.

18. The apparatus of claims 13, 14 or 15 in which: said housing outer surface is textured for interacting with urethral tissue to releasibly hold said housing in the urethra.

19. In bladder control apparatus adapted to be placed in a urethra and including a valve block having a valve with open and closed positions and a fluid flow path through the valve block, the method of controlling fluid flow comprising the steps of:

a. normally biasing the valve in the closed position;

b. moving the valve to the open position when the hydrostatic pressure in the urethra exceeds a predetermined level;

c. inducing a negative pressure from means in the fluid flow path according to Bernoulli's principle;

d. holding the valve in the open position with the negative pressure; and e. moving the valve to the closed position when the induced negative pressure falls below the normal biasing pressure.

20. In bladder control apparatus adapted to be placed in a urethra and including a valve block having a valve with open and closed positions and a fluid flow path through the valve block, the method of controlling fluid flow comprising the steps of:

a. normally biasing the valve in the closed position;

b. moving the valve to the open position when the hydrostatic pressure in the urethra exceeds a predetermined level;

c. increasing the surface area of impingement of the fluid flow on means in the flow path to create a valve holding pressure;

d. holding the valve in the open position with the valve holding pressure; and e. moving the valve to the closed position when the valve holding pressure falls below the normal biasing pressure.

21. The method of claims 19 or 20 including the step of: preventing movement of the normally closed valve due to an abrupt change in the urethral hydrostatic pressure.

22. An intraurethral bladder control apparatus comprising:

a. a housing for removable attachment within a urethra; and b. valve means coupled to said housing for controlling fluid flow through said urethra, upon exposure to a predetermined pressure said valve means opening to initiate fluid flow, said valve means remaining open under the influence of a holding force according to Bernoulli's principle and said fluid flow continuing through said urethra at a pressure less than said predetermined pressure.

23. An intraurethral bladder control apparatus according to claim 22 further comprising means coupled to said housing for resetting said initiating and continuing means to a state which prevents further fluid flow through said urethra until renewed exposure to said predetermined pressure.

* * * * *